United States Patent
Klorg

(10) Patent No.: US 9,409,036 B2
(45) Date of Patent: Aug. 9, 2016

(54) IMPLANTABLE CONNECTOR SYSTEMS HAVING MAGNETIC PORTIONS THEREON AND RELATED METHODS

(75) Inventor: David Klorg, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 13/185,933

(22) Filed: Jul. 19, 2011

(65) Prior Publication Data

US 2012/0016429 A1    Jan. 19, 2012

Related U.S. Application Data

(60) Provisional application No. 61/365,508, filed on Jul. 19, 2010.

(51) Int. Cl.
*A61N 1/00* (2006.01)
*A61N 5/06* (2006.01)

(52) U.S. Cl.
CPC .............. *A61N 5/0601* (2013.01); *A61N 5/062* (2013.01); *A61N 5/0622* (2013.01); *A61N 2005/063* (2013.01); *A61N 2005/0612* (2013.01)

(58) Field of Classification Search
CPC .................. A61B 2018/00434; A61N 1/0529; A61N 1/0534; A61N 1/0539; A61N 1/375; A61N 2005/0612; A61N 2005/063; A61N 5/0601
USPC ............ 607/1, 2, 46, 59, 88, 116; 604/20, 21; 600/378
See application file for complete search history.

(56) References Cited

U.S. PATENT DOCUMENTS

| 4,109,998 | A |   | 8/1978  | Iverson |
|---|---|---|---|---|
| 4,124,272 | A |   | 11/1978 | Henderson et al. |
| 5,073,040 | A |   | 12/1991 | Guinard |
| 5,157,745 | A |   | 10/1992 | Ames |
| 5,371,814 | A |   | 12/1994 | Ames et al. |
| 6,301,405 | B1 |   | 10/2001 | Keil |
| 6,980,714 | B2 |   | 12/2005 | Lo et al. |
| 7,548,775 | B2 | * | 6/2009  | Kipke et al. ............... 600/378 |
| 2008/0091248 | A1 | * | 4/2008 | Libbus et al. ............... 607/60 |
| 2008/0305649 | A1 | * | 12/2008 | Didur et al. ................. 439/39 |
| 2010/0195956 | A1 |   | 8/2010 | Zhang et al. |
| 2011/0125078 | A1 | * | 5/2011 | Denison et al. ............. 604/20 |

OTHER PUBLICATIONS

Catalog, Photonics Hardwareproduts for Optogenetics, Jan. 2011, www.doriclenses.com, 44 pages.

* cited by examiner

*Primary Examiner* — Niketa Patel
*Assistant Examiner* — Lindsey G Hankins
(74) *Attorney, Agent, or Firm* — Myers Bigel & Sibley, PA

(57) ABSTRACT

A connecting system includes an implantable base unit having an implantable housing with an externally accessible magnetic portion and an implantable unit connecting member. The implantable base unit is configured to be at least partially implanted in a subject such that the externally accessible magnetic portion is accessible from an external region of the subject. An interface unit is releasably coupled to the implantable base unit. The interface unit has an interface housing with an interface magnetic portion and an interface unit connecting member. The interface magnetic portion is configured to engage the externally accessible magnetic portion of the implantable base unit to mechanically couple the implantable unit connecting member and the interface unit connecting member.

15 Claims, 16 Drawing Sheets

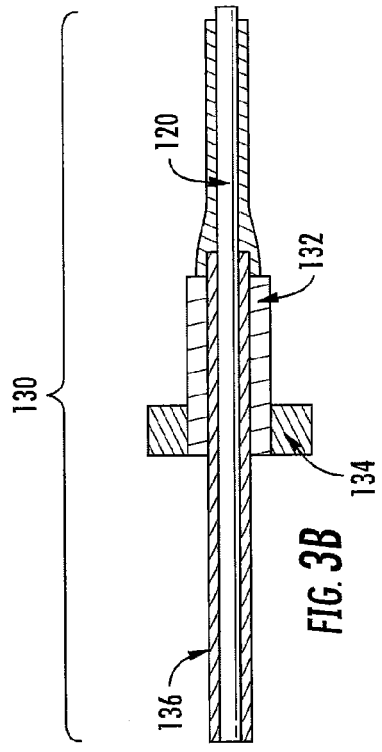
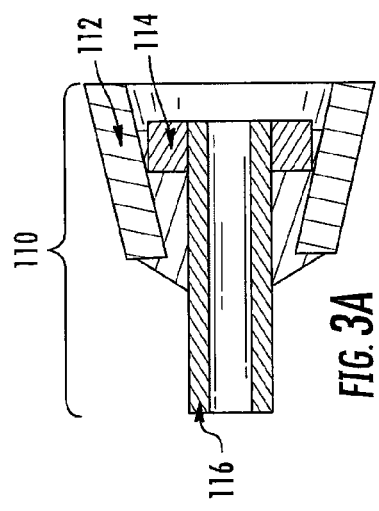
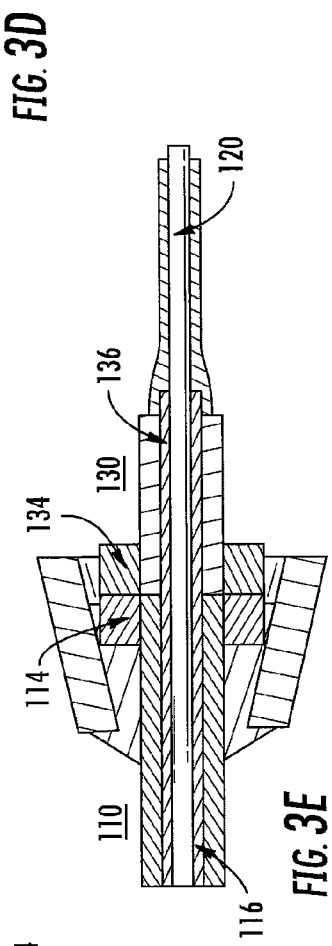
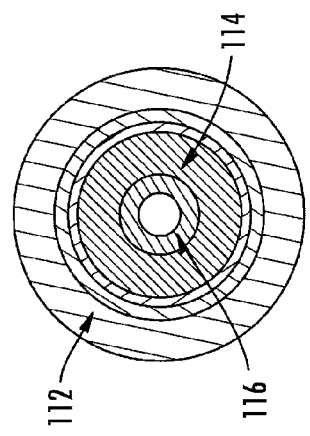

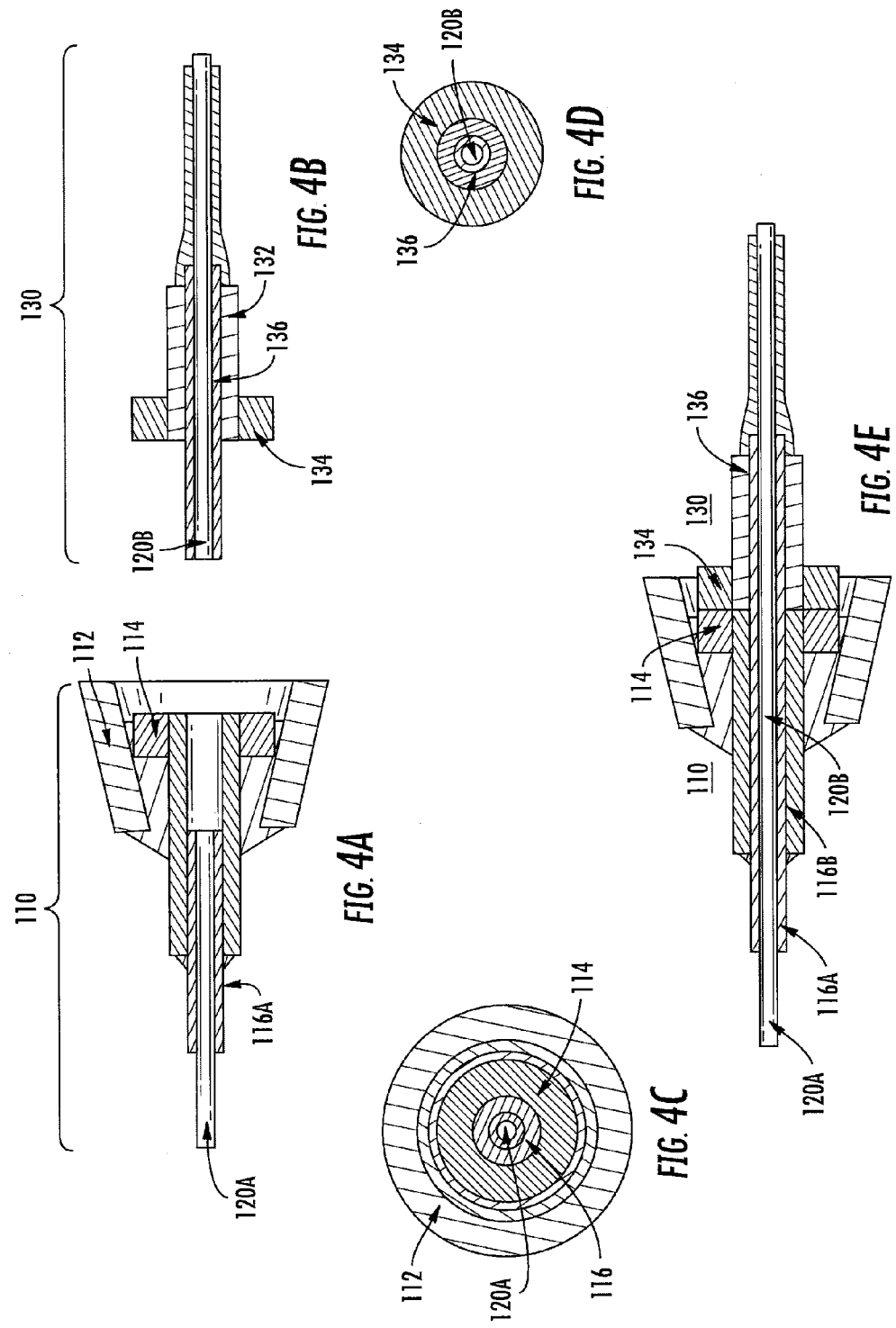

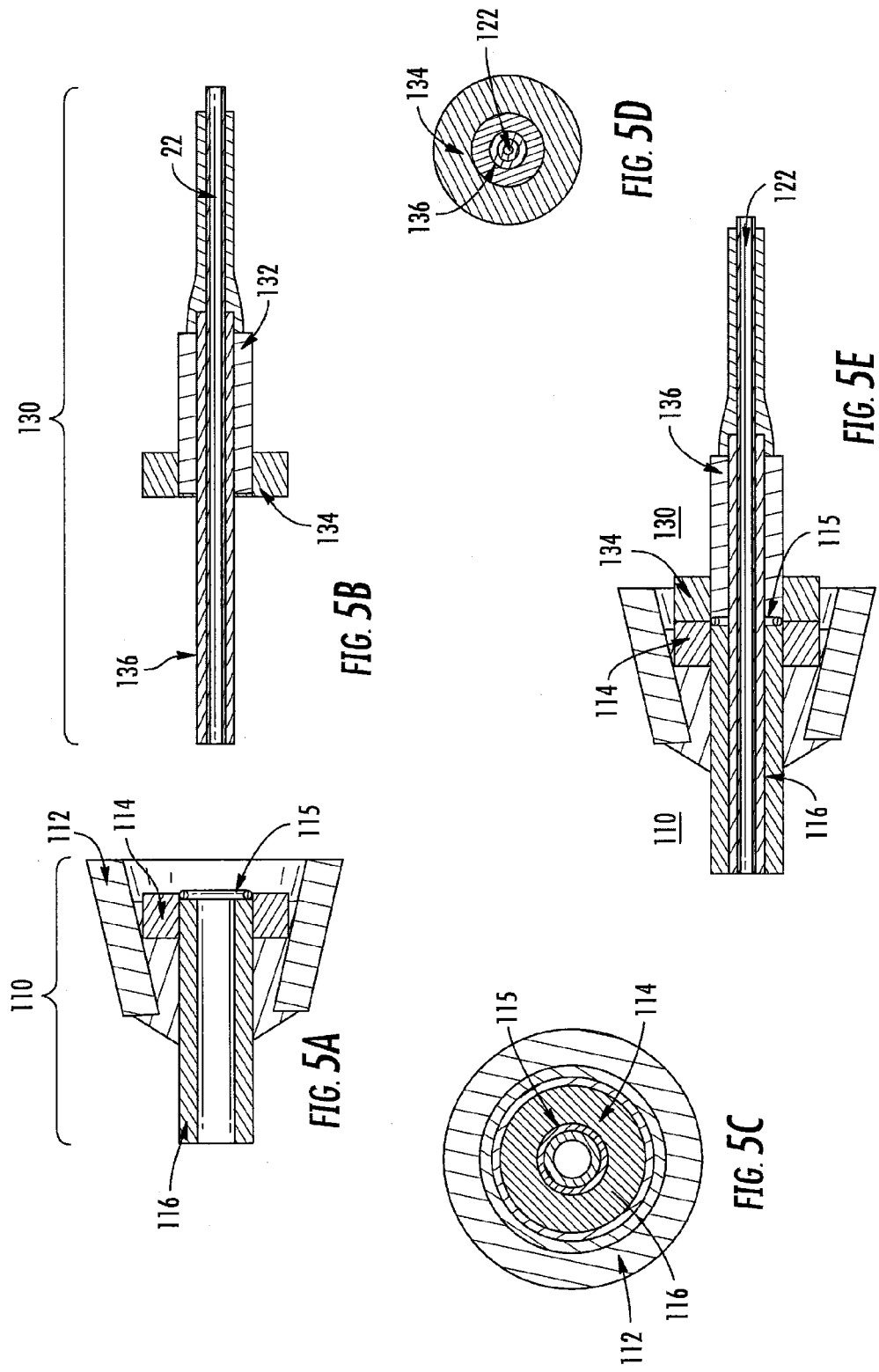

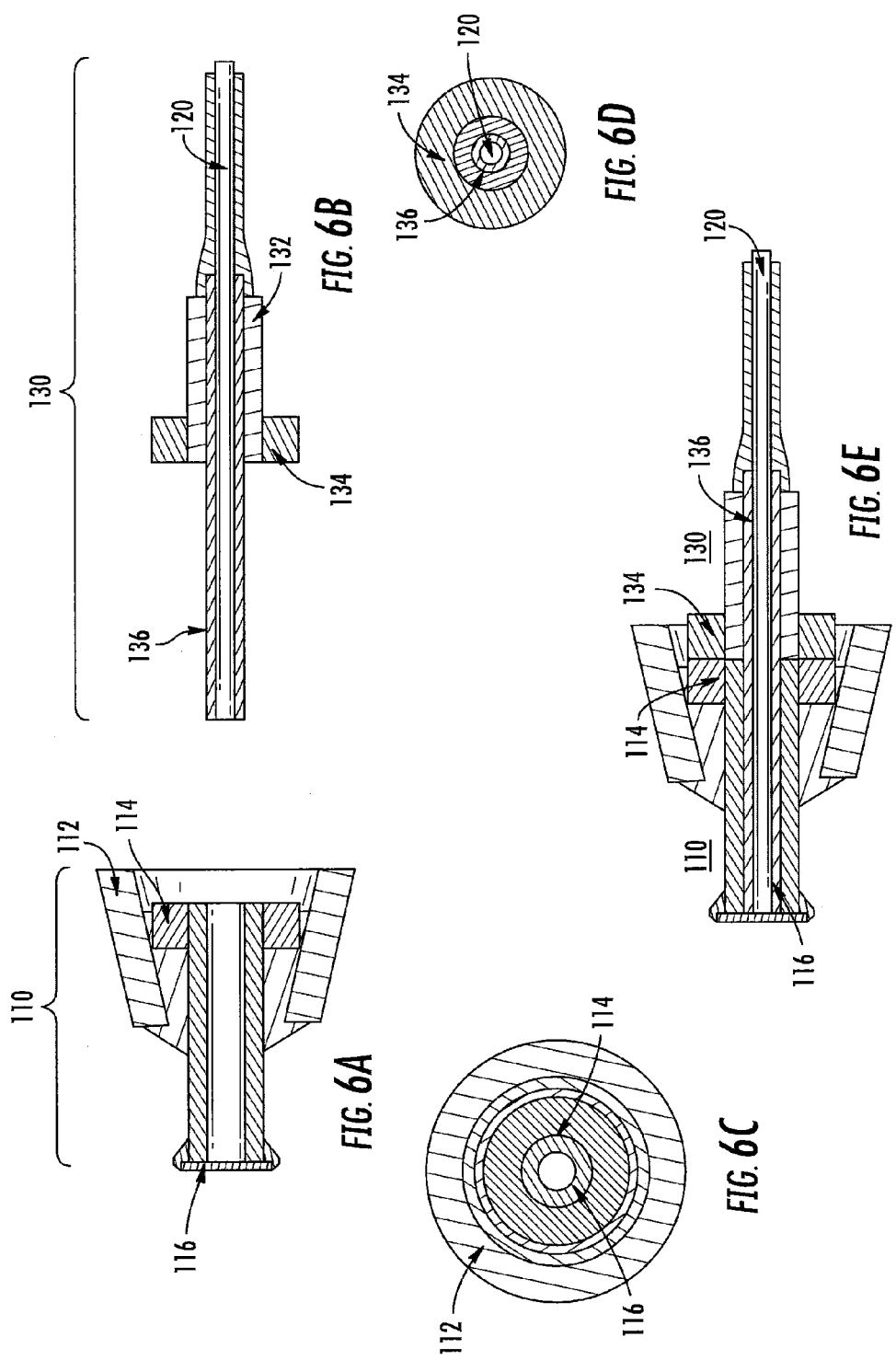

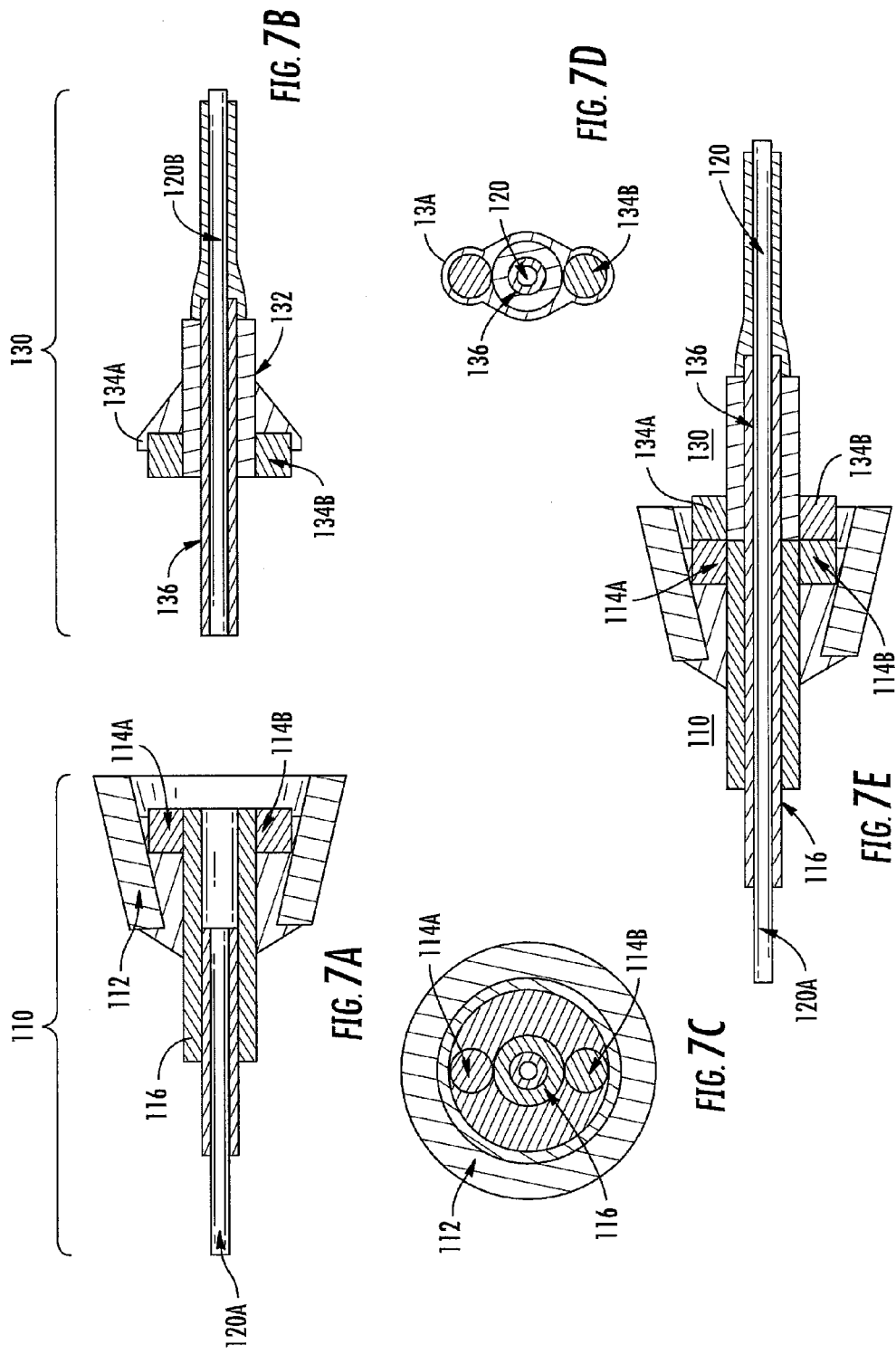

IMPLANTABLE CONNECTOR SYSTEMS HAVING MAGNETIC PORTIONS THEREON AND RELATED METHODS

RELATED APPLICATIONS

This applications claims priority to U.S. Provisional Application Ser. No. 61/365,508, filed Jul. 19, 2010, the disclosure of which is incorporated by reference in its entirety.

GOVERNMENT RIGHTS

This invention was made with Government support under agreement number 5R21EY018159-02, awarded by the National Eye Institute. The Government has certain rights in the invention.

FIELD OF THE INVENTION

The present invention relates to implantable connectors, and in particular, connectors that connect implantable cannulas or electrical devices to external devices.

BACKGROUND

Optogenetics is a promising new technique in neuroscience, combining optical and genetic techniques to probe neural circuits. It relies on microbial opsins, light sensitive proteins, to manipulate the activity of neurons in response to flashes of light. New genetic techniques developed in parallel allow neuroscientists the ability to select specific types of neurons for optogenetic control. By perturbing the activity of specific neurons in live animals, neuroscientists can determine the role that the neurons play in the expression of behavior. In addition, optogenetic techniques developed to study the brain in the lab may be useful in treating a wide range of neurological disorders in the clinic. In order to move optogenetics from the proof-of-principle stage to routine use in the lab and the clinic, a set of optimized techniques and equipment need to be developed.

In order to optically stimulate the brain of freely moving animals, drug delivery cannula systems have been re-purposed to allow an optical fiber to pass through a guide cannula that is implanted through the skull of the animal. The guide cannula is typically connected to a pedestal, which is mounted on the head of the animal using a screw interface, cranioplastic cement, dental cement and/or other bonding materials. Threading or clips may be used to attach the guide cannula to an external device. The screw type connection used to hold the fiber in place in these systems does not allow for free rotation and can be difficult to connect to un-anaesthetized animals. Optical fibers are more fragile than the fluid delivery cannula these systems were designed for and as a result, fiber breakage is a common problem. In addition, the guide cannula is open to the brain, allowing the entry of blood and fluid into the cannula and bacterial contamination into the brain from external sources. With chronic stimulation, repeated insertion and withdrawal of the fiber and dummy plug can damage the brain structure under study.

In addition, neurophysiologists have used acute single electrode recordings in anesthetized animals to study neurons in the brain. More recently, chronic multi-electrode recordings in awake, behaving animals have been used due, in part, to the realization that many neural systems behave very differently in the anesthetized brain. Neuro-engineers first hand-built electrode assemblies, and as the technique gained acceptance, several companies (such as Plexon, Inc., Dallas, Tex., U.S.A.) have commercialized multi-electrode assemblies and equipment. A significant enhancement in the quality of chronic recordings came with the invention of headstage amplifiers. These tiny printed circuits may be situated directly on the head of the animal to boost and condition neural signals prior to sending them through a cable to the main amplifiers. Headstage amplifiers may be used to interface high impedance electrodes with low impedance cables and also to boost gain. Thus, headstages are now standard equipment for chronic recording experiments. However, the connectors that are typically used to connect the headstage to the implanted electrodes may be highly susceptible to the stresses of head movement in an awake animal despite being small and lightweight. Thus, when the connector flexes, the electrical contacts may move and generate noise which overwhelms the neural signal. For studying behavioral tasks that may involve movement, the noise may be a significant problem to obtaining useful data.

SUMMARY OF EMBODIMENTS OF THE INVENTION

In some embodiments, a connecting system includes an implantable base unit having an implantable housing with an externally accessible magnetic portion and an implantable unit connecting member. The implantable base unit is configured to be at least partially implanted in a subject such that the externally accessible magnetic portion is accessible from an external region of the subject. An interface unit is releasably coupled to the implantable base unit. The interface unit has an interface housing with an interface magnetic portion and an interface unit connecting member. The interface magnetic portion is configured to engage the externally accessible magnetic portion of the implantable base unit to mechanically couple the implantable unit connecting member and the interface unit connecting member.

In some embodiments, the implantable unit connecting member comprises an implantable cannula configured to receive the interface unit connecting member therein.

In some embodiments an implantable optical fiber is in the implantable cannula. The implantable optical fiber may be configured to optically stimulate a portion of a brain of the subject. The interface optical fiber is configured to connect to an external light source and to provide a light passageway for light from the external light source to the implantable optical fiber. In some embodiments, an interface optical fiber is in the interface cannula and is configured to transmit light to the implantable optical fiber when the interface unit is connected to the implantable unit.

In some embodiments, an implantable optical interface, window, or lens is mounted on the terminal end of the implanted cannula.

In some embodiments, the interface unit is rotatably coupled to the implantable base unit by the interface magnetic portion and the externally accessible magnetic portion.

In some embodiments, a buffer member is on the interface unit and is configured to provide a buffer region around the interface magnetic portion and the externally accessible magnetic portion.

In some embodiments, the implantable cannula is configured to receive a fluid therein.

In some embodiments, the implantable base unit further comprises an implantable electrode assembly configured to be implanted in or adjacent to neural tissues in the subject, and the interface unit further comprises an external electrode assembly configured to electrically connect to the implantable electrode assembly when the interface magnetic portion engages the externally accessible magnetic portion of the implantable base unit.

In some embodiments, the implantable housing comprises a first implantable housing, the externally accessible magnetic portion comprises a first magnetic portion, the implantable unit connecting member comprises a first implantable unit connecting member, the interface housing comprises a first interface housing, the interface magnetic portion comprises a first interface magnetic portion and the interface unit connecting member comprises a first interface unit connecting member. The implantable base unit may include a second implantable housing with a second externally accessible magnetic portion and a second implantable unit connecting member. The interface unit may include a second interface housing with a second interface magnetic portion thereon and a second interface unit connecting member. The second interface magnetic portion may be configured to engage the second externally accessible magnetic portion of the implantable base unit to mechanically couple the second implantable unit connecting member and the second interface unit connecting member.

In some embodiments, implantable electrode assembly is mounted on the implantable unit between the first and second implantable unit connecting members and the external electrode assembly is mounted on the interface unit between the first and second interface unit connecting members.

The first and second implantable housings may be rigidly connected. The first and second interface housings may be rigidly connected. The external electrode assembly may include an amplifier.

In some embodiments, a connection method includes providing an implantable base unit having an implantable housing with an externally accessible magnetic portion and an implantable unit connecting member. An interface unit having an interface housing with an interface magnetic portion and an interface unit connecting member is provided. The externally accessible magnetic portion of the implantable base unit is engaged with the interface magnetic portion to couple the implantable unit connecting member and the interface unit connecting member. The implantable base unit is configured to be at least partially implanted in a subject such that the externally accessible magnetic portion is accessible from an external region of the subject.

In some embodiments, a connection method includes implanting an implantable base unit in a subject. The implantable base unit has an implantable housing with an externally accessible magnetic portion and an implantable unit connecting member. The externally accessible magnetic portion is accessible from an external region of the subject. An interface unit is connected to the implantable unit. The interface unit has an interface housing with an interface magnetic portion and an interface unit connecting member. The interface magnetic portion engages the externally accessible magnetic portion of the implantable base unit to mechanically couple the implantable unit connecting member and the interface unit connecting member.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3A is a cross-sectional side view of an implantable base unit of a connecting system according to some embodiments of the invention.

FIG. 3B is a cross-sectional side view of an interface unit that is configured to releaseably connect to the implantable base unit of FIG. 3A to form a connecting system according to some embodiments of the invention.

FIG. 3C is a top view of the implantable base unit of FIG. 3A.

FIG. 3D is a top view of the interface unit of FIG. 3B.

FIG. 3E is a cross-sectional side view of the implantable base unit of FIG. 3A connected to the interface unit of FIG. 3B.

FIG. 4A is a cross-sectional side view of an implantable base unit of a connecting system according to some embodiments of the invention.

FIG. 4B is a cross-sectional side view of an interface unit that is configured to releaseably connect to the implantable base unit of FIG. 4A to form a connecting system according to some embodiments of the invention.

FIG. 4C is a top view of the implantable base unit of FIG. 4A.

FIG. 4D is a top view of the interface unit of FIG. 4B.

FIG. 4E is a cross-sectional side view of the implantable base unit of FIG. 4A connected to the interface unit of FIG. 4B.

FIG. 5A is a cross-sectional side view of an implantable base unit of a connecting system according to some embodiments of the invention designed for fluid delivery.

FIG. 5B is a cross-sectional side view of an interface unit that is configured to releaseably connect to the implantable base unit of FIG. 5A to form a connecting system according to some embodiments of the invention.

FIG. 5C is a top view of the implantable base unit of FIG. 5A.

FIG. 5D is a top view of the interface unit of FIG. 5B.

FIG. 5E is a cross-sectional side view of the implantable base unit of FIG. 5A connected to the interface unit of FIG. 5B.

FIG. 6A is a cross-sectional side view of an implantable base unit of a connecting system according to some embodiments of the invention.

FIG. 6B is a cross-sectional side view of an interface unit that is configured to releaseably connect to the implantable base unit of FIG. 6A to form a connecting system according to some embodiments of the invention.

FIG. 6C is a top view of the implantable base unit of FIG. 6A.

FIG. 6D is a top view of the interface unit of FIG. 6B.

FIG. 6E is a cross-sectional side view of the implantable base unit of FIG. 6A connected to the interface unit of FIG. 6B.

FIG. 7A is a cross-sectional side view of an implantable base unit of a connecting system according to some embodiments of the invention.

FIG. 7B is a cross-sectional side view of an interface unit that is configured to releaseably connect to the implantable base unit of FIG. 7A to form a connecting system according to some embodiments of the invention.

FIG. 7C is a top view of the implantable base unit of FIG. 7A.

FIG. 7D is a top view of the interface unit of FIG. 7B.

FIG. 7E is a cross-sectional side view of the implantable base unit of FIG. 7A connected to the interface unit of FIG. 7B.

DETAILED DESCRIPTION OF EMBODIMENTS OF THE INVENTION

Figure 1:
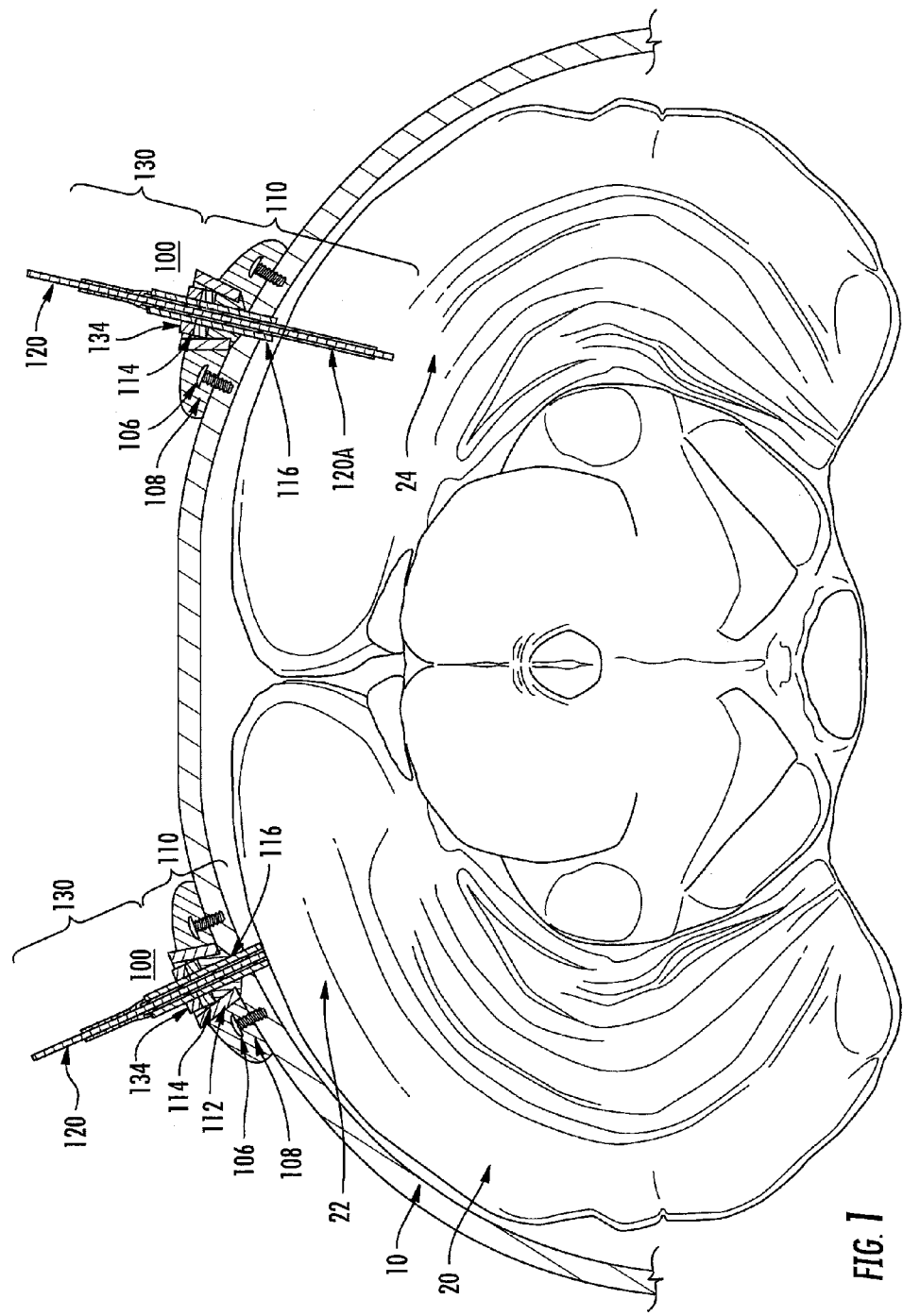
FIG. 1 is a cross-sectional view of connecting systems according to some embodiments of the invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the term "implant" refers to fixing a medical device on or in a subject's body. Thus, an "implantable" device may be partially implanted or may be fixed to an external portion of the subject's body such that all or a portion of the device is positioned on the exterior of the subject's body. For example, in some embodiments, an "implantable" device may be affixed to the skull, and an "implantable" connecting member (such as a cannula, socket or post or other interlocking configuration) may be connected to an implantable device with or without actually extending into the subject's body. In some embodiments, portions of the device may be formed of a biocompatible material.

Embodiments according to the present invention may be used with veterinary and human subjects. Subjects may include human or non-human animal subjects, particularly mammalian subjects such as canines, felines, bovines, caprines, equines, ovines, porcines, rodents (e.g., rats and mice), lagomorphs, non-human primates, etc., for, e.g., medical, veterinary medical and/or laboratory research purposes.

As illustrated in FIG. 1, connecting systems 100 may be partially implanted, e.g., through a skull 10 and on or in a brain 20 of a subject. As shown, the connecting system 100 includes an implantable base unit 110 and an interface unit 130.

As illustrated in FIGS. 1-7, the implantable base unit 110 includes an implantable housing 112 having an externally accessible magnetic portion 114 thereon. An implantable cannula 116 extends through the housing 112. The implantable base unit 110 is configured to be at least partially implanted in a subject such that a portion of the implantable cannula 116 extends into the subject as shown in FIG. 1, and the externally accessible magnetic portion 114 is accessible from an external region of the subject. As further shown in FIG. 1, the implantable housing 112 is surgically implanted and affixed to the skull 10 by surgical fasteners, such as screws 106, and/or biocompatible adhesive such as dental cement 108. The interface unit 130 is releasably coupled to the implantable base unit 110.

As shown in FIGS. 1-6, the interface unit 130 includes an interface housing 132 having an interface magnetic portion 134 thereon. An interface cannula 136 extends through the housing 132. The interface magnetic portion 134 is of a polarity that is opposite the magnetic portion 114 such that the interface magnetic portion 134 attracts and engages the externally accessible magnetic portion 114 of the implantable base unit 110. As shown in FIGS. 3A-3B and in FIGS. 4A-4B, the interface unit 130 may be removed from the cooperating housing 112 of the implantable unit 110. As shown in FIG. 3E and FIG. 4E, the interface magnetic portion 134 and the externally accessible magnetic portion 114 may form a magnetic connection to couple the interface unit 130 and the implantable unit 110. As illustrated, the implantable cannula 116 and the interface cannula 136 are coupled to form a generally continuous cannula from the interface unit 130 to the implantable unit 110 when the interface unit 130 and the implantable unit 110 are connected as shown in FIGS. 1, 2, 3E, 4E, 5E, and 6E.

Connecting systems according to embodiments of the present invention may be used for a variety of applications. For example, the implantable cannula 116 and interface cannula 136 may be used to insert an optical fiber as described herein and as illustrated by an optical fiber 120 in FIGS. 1, 2, 3A-3E, and 6A-6E and optical fibers 120A, 120B in FIGS. 4A-4E and 7A-7E. In some embodiments, the implantable cannula 116 and interface cannula 136 may be used for fluid delivery systems, such as a drug delivery system. As shown in FIGS. 5A-5E, a fluid delivery tube 122 may be used to deliver fluid to the subject via the implantable cannula 116. The fluid delivery tube 122 may be connected to a fluid source, which may include an active agent such as a therapeutic agent or drug (not shown). As shown in FIGS. 5A-5E, a sealing member 115, such as an O-ring, may be used to provide a seal around the implantable cannula 116 to facilitate fluid flow and reduce leakage. Accordingly, the implantable cannula 116 may be used to transport fluid to a subject, such as in a drug delivery system, and the sealing member 115 provides a fluid seal between the implantable cannula 116 and the interface cannula 136, which contains or connects to the flexible fluid delivery tubing 122.

The implantable cannula 116 may be accessible to an external device (such as a fluid source for a fluid delivery system or a light source for optical probes as typically used in optogenetics research) via the interface unit 130 and interface cannula 136. When access to the implantable cannula 116 is not needed, the interface unit 130 may be removed. In addition, the externally accessible magnetic portion 114 and the interface magnetic portion 134 may permit generally free rotation of the interface unit 130 with respect to the implantable unit 110. In some embodiments, a lubricant, such as petroleum jelly, may be used to facilitate rotation of the interface unit with respect to the implantable unit 110. Thus, the subject in which the implantable unit 110 is implanted may move with increased freedom with respect to any connections to the interface cannula 136, such as fluid passageways or fiber optics that may be connected to the cannula 136.

In some embodiments, as shown in FIG. 6A, the implantable unit 110 includes an implantable cap or window 118, which serves as a barrier for reducing infection and/or fluid flow. The cap 118 may be formed of a transparent material, such as glass or polymeric material, and may facilitate the optical transmissions of the optical fiber 120 to the brain 20 as shown in FIG. 1. As shown in FIG. 6A-6E, the optical fiber 120 may be attached to the interface unit 110 and inserted into the implantable unit 130. The implantable cap may also be a micro-lens which serves to modify the optical path and change the area of illumination.

Figure 2:
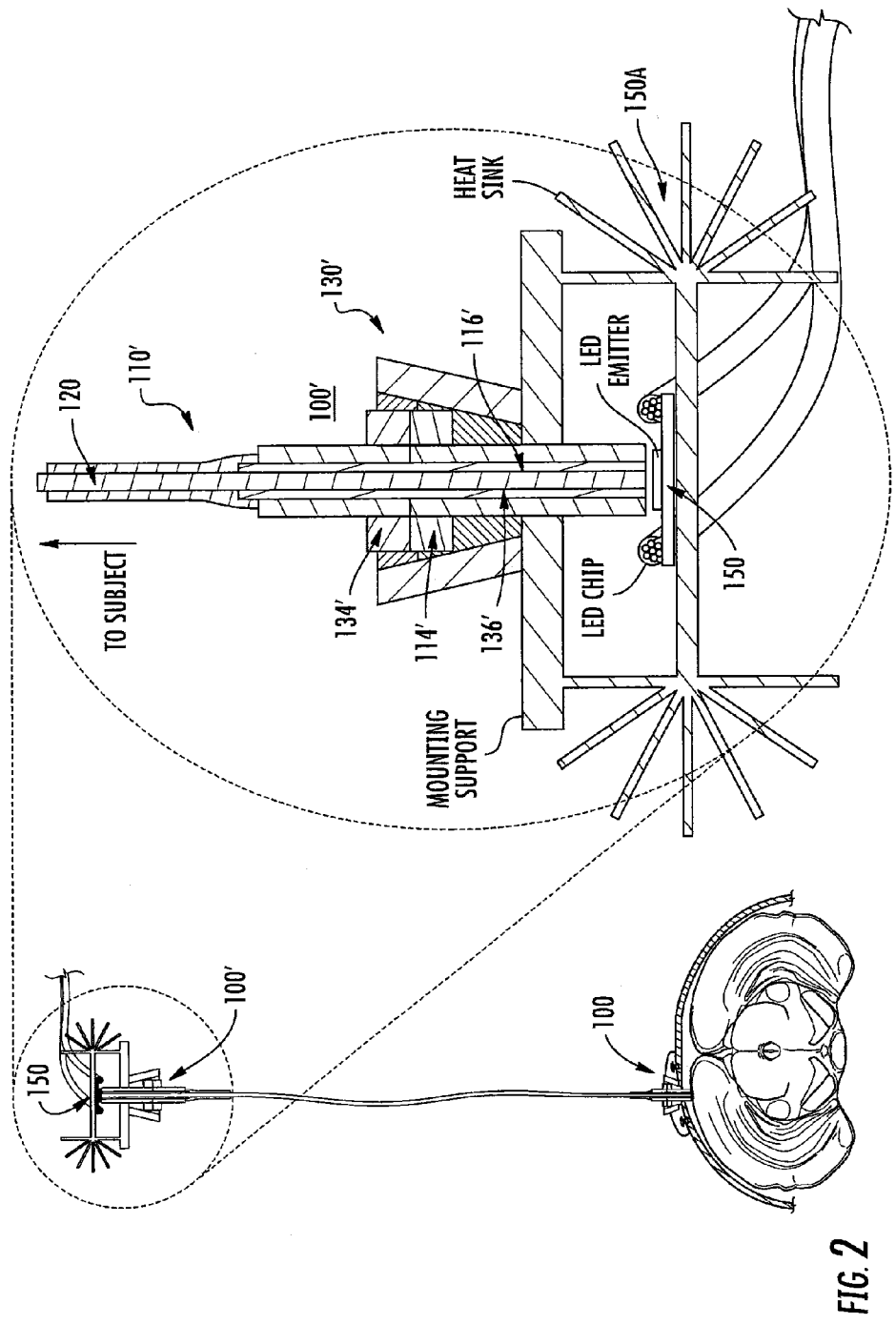
FIG. 2 is a cross-sectional side view of a magnetic connecting system connected to a light source according to some embodiments of the invention.

The cannulas 116, 136 may be used for various medical and/or research applications in animal or human subjects, such as implantable optical fibers, fluid delivery systems (e.g. microdialysis probes), drug delivery devices, and/or for the delivery or removal of a fluid. For example, in some embodiments, a light guide or optical fiber 120 is provided in the cannulas 116, 136. As illustrated in FIG. 2, a light source, such as an LED emitter 150 may be coupled to the outer end of the interface fiber 120 via an LED connector 100' so that light from the LED emitter 150 may be transmitted from the LED emitter, through the optical fiber and directed into the subject, such as into the cortical region 22 or deep structure regions 24. As shown in FIG. 2, the LED connector 100' includes an LED source unit 110' and an interface unit 130' having respective magnetic portions 114', 134' and cannula 116', 136' for contacting the optical fiber 120' to the LED emitter 150. The LED source unit 110' is connected to a housing 150A of the LED emitter 150. In this configuration, the interface unit 130' is releasably connected to the LED source unit 110' via the magnetic portions 114', 134' so that the interface unit 130' may be connected to different ones of a plurality of LED emitters (not shown) to provide, e.g., different LED sources of different wavelengths. The light from the LED emitter 150 is transmitted via the optical fiber 120 to the implantable connector 100, which is implanted in the subject as shown in FIG. 2.

Although the LED emitter 150 is illustrated with respect to the housing 150A and LED connector 100', it should be understood that any suitable light source may be used, and the light source may be coupled to the optical fiber 120 using any suitable coupling technique, the selection of which is known to those of skill in the art.

As illustrated in FIGS. 1-2, the connection system 100 may be used to provide an implantable optical fiber, for example, for optogenetic research in which light-sensitive agents such as microbial opsins are used to manipulate the activity of neurons in living animals in response to flashes of light. The implantable unit 110 is chronically implanted in the brain of a research subject as shown in FIG. 1, and the interface unit 130 is releasably connected thereto. Moreover, the interface unit 130 may rotate with respect to the implantable unit 110 to reduce twisting of an optical fiber extending from the interface unit 130 and away from the subject. In some embodiments, a buffer material may be used to reduce the likelihood of or prevent the magnet from coming into contact with external ferromagnetic materials, e.g., on the outside of the interface unit 130 to reduce the magnetic attachment in the region around the interface unit 130 to reduce or prevent the implantable unit 110 and interface unit 130 from being magnetically attracted to objects other than the magnetic portions 114, 134.

In some embodiments, the implantable cannula 116 extends to the cortical region 22 of the brain 20 for optical stimulation of the cortical region via an optical fiber 120. However, the implantable cannula 116 may be sized and configured for access to any desired region. For example, in some embodiments as shown in FIG. 1, the implantable cannula 116 is sized and configured for accessing deep structure regions 24 of the brain 20. As illustrated, an implantable fiber 120A is contained within the implantable cannula 116.

Although embodiments of the present invention are illustrated herein with respect to implantable cannulas positioned in or near the brain, it should be understood that the implantable cannula 116 may be attached to bony structures such as the skull and spinal cord, or sutured or otherwise attached to the skin for access to organs such as the heart, kidney, liver, or lungs, or for arterial and venous cannulation.

Figure 8C:
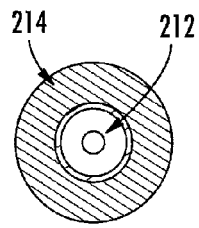
FIG. 8C is a top view of the protective cover of FIGS. 8A-8B.
Figure 8A:
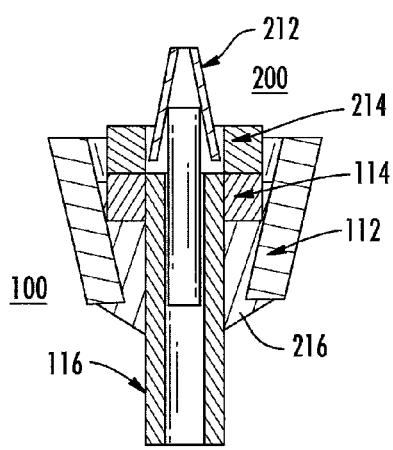
FIG. 8A is a cross-sectional side view of an implantable base unit and a protective cover in an closed configuration according to some embodiments of the present invention.
Figure 8B:
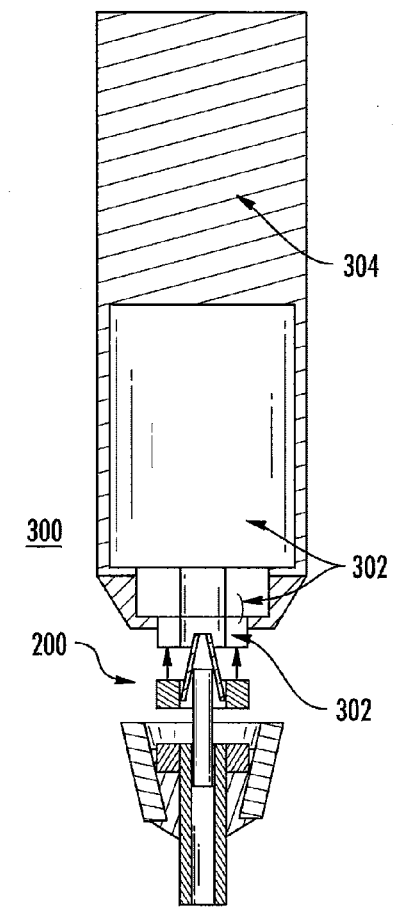
FIG. 8B is a side view of an extraction tool for removing the protective cover of FIG. 8A.

In some embodiments, optical fibers may be provided in both the implantable base unit 110 and the interface unit 130. As illustrated in FIG. 4A-4E and FIGS. 7A-7E, the implantable base unit 110 may include an implantable optical fiber 120A, and the interface unit 130 may include an interface optical fiber 120B. In this configuration, the optical fiber 120A is implanted in the subject, and the optical fiber 120B is configured to optically couple to the optical fiber 120A, as shown in FIG. 4E, for light transmission. As illustrated in FIGS. 8A-8C, a protective cover or cap 200 may be used when the interface unit 130 is not being used to connect the implantable cannula 116 to another device. The protective cap 200 may include a buffer 212 (e.g., a buffer formed from plastic or other non-magnetic material) with a magnetic or ferromagnetic metal portion 214 and an insert 216. As shown in FIG. 8B, the magnetic portion 214 forms a magnetic connection with the magnetic portion 114 of the implantable unit 110, and the insert 216 is configured to be inserted into the implantable cannula 116. As shown in FIG. 8C, the protective cap 200 may be removed from the implantable unit 110 with an extraction tool 300, e.g., so that the interface unit 130 may be connected to the implantable unit 110. The extraction tool 300 includes strong extraction magnets 302 that are connected to the protective cap magnet or other ferromagnetic material 212 and a handle 304 (e.g., a handle formed from plastic or other non-magnetic material) for withdrawing the cap 200 from the implantable unit 110. Accordingly, the interface unit 130 may be removed from the implantable base unit 110 and the removable cap 200 is positioned in the implantable base unit 110 such that the implantable cannula 116 is covered by the cap 200. As illustrated, the portion 214 is accessible to the strong extraction magnet 302, which is sufficiently strong so as to engage the portion 214 and to remove the cap 200 when the extraction tool 300 is moved away from the implantable base unit 110.

Although embodiments according to the present invention are illustrated with respect to the cap 200 and extraction tool 300, it should be understood that other configurations may be used. For example, the cap 200 may include any suitable feature, such as an aperture, that is configured to mate with a corresponding feature, such as a hook, on the extraction tool 300.

Although embodiments according to the present invention are illustrated with respect to an interface unit 130 that is inserted into and received in a housing 112 of the implantable unit 110, it should be understood that other configurations may be used. For example, the implantable unit 110 and the housing 132 of the interface unit 130 may be configured so that the implantable unit 110 is received in the housing 132 of the interface unit 130 without departing from the scope of the invention. The magnetic portions 114, 134 and 214 may be formed of ring-shaped neodymium magnets; however, other permanent or temporary magnetic materials may be used. Moreover, other suitable shapes of magnetic portions may be used.

As shown in FIGS. 4A-4E and FIGS. 7A-7E, the optical fibers 120A, 120B may be aligned using precision manufacturing. However, typical tolerances of commercially available stainless steel hypodermic tubing, which may be used to provide the cannula 116, 136, may not be sufficiently small so as to ensure perfect centering and coupling of the ends of the optical fibers 120A, 120B. In some embodiments, the interface optical fiber 120B may be larger than the implantable optical fiber 120A so that, even if the optical fibers 120A, 120B are not in perfect alignment, sufficient light is transmitted due to increased output intensity at the tip of the interface optical fiber 120B. In some embodiments, a magnetic couple may be provided that allows for manual rotation, but will lock into a connected position at a particular position or angle, e.g., as shown in FIGS. 7A-7E, so that the position of the interface unit 130 may be fixed with respect to the implantable unit 110.

For example, as illustrated in FIGS. 7A-7E, circular-shaped magnetic portions 114A, 114B and 134A, 134B may be used, such as when rotation of the interface unit 130 with respect to the implantable unit 110 is not generally desired or is desired only with manual rotation. As shown, the magnet portions 114A, 114B are of opposite polarity, and the magnetic portions 134A, 134B are of opposite polarity such that the magnetic portion 114A is magnetically attracted to the magnetic portion 134A (but is repelled by the magnetic portion 134B) and the magnetic portion 114B is magnetically attracted to the magnetic portion 134B (but is repelled by the magnetic portion 134A). In this configuration as shown in FIGS. 7A-7E, the position of the interface unit 130 and the implantable unit 110 will generally lock in the position shown in FIG. 7E, and the interface unit 130 is rotatable with manual rotation. Accordingly, the optical fibers 120A, 120B may be aligned during the manufacturing process with respect to the fixed angle, which may require a lower degree of precision manufacturing than if full rotational movement is allowed.

In some embodiments, the cannulas 116, 136 may be sized and configured for a specific size of optical fiber, for example, to accommodate optical fibers with a diameter of about 100 um to about 1 mm. The cannulas may be formed of any suitable material, including stainless steel or other biocompatible materials. The implantable unit 110 and/or interface unit 130 may be formed of materials that are compatible with sterilization solutions, such as ethylene-oxides. The pull strengths of the magnetic portions 114, 136, 114A, 114B, 134A and 134B may be selected to allow for ease and/or speed of connection and disconnection while maintaining a sufficiently secure connection during use, typical pull strengths are around 0.36 lbs/in$^2$ or between about 0.4 and about 0.5 lbs/in$^2$.

Although embodiments according to the present invention are described herein with respect to an implantable unit 110 and an interface unit 130, the magnetic connector units may be configured for other applications, such as on hand held devices, including disposable light delivery probes for hand-held light sources in medical and dental uses, fluid carrying lines, etc. For example, a plurality of female connectors analogous to the implantable unit may be positioned in a chemical reaction manifold, and a user may take multiple spectroscopic readings using a magnetically mating handheld device that magnetically connects to the female connectors. The connectors according to embodiments of the present invention may also be used to chronically deliver drug or biologicals to the brain or other organs.

Embodiments according to the invention may facilitate the placement or connection of fiber optics, and such systems may also be used with fiber bundles (i.e., IGN-06/17, Sumitomo Electric Industries), for chronic endoscopic imaging of brain tissue or other organs. In addition the guide cannula and connector may be used to record electroencephalograph (EEG) signals from the brain or combined with traditional implanted recording electrodes to monitor ongoing brain activity from both single neurons and populations.

Figure 9B:
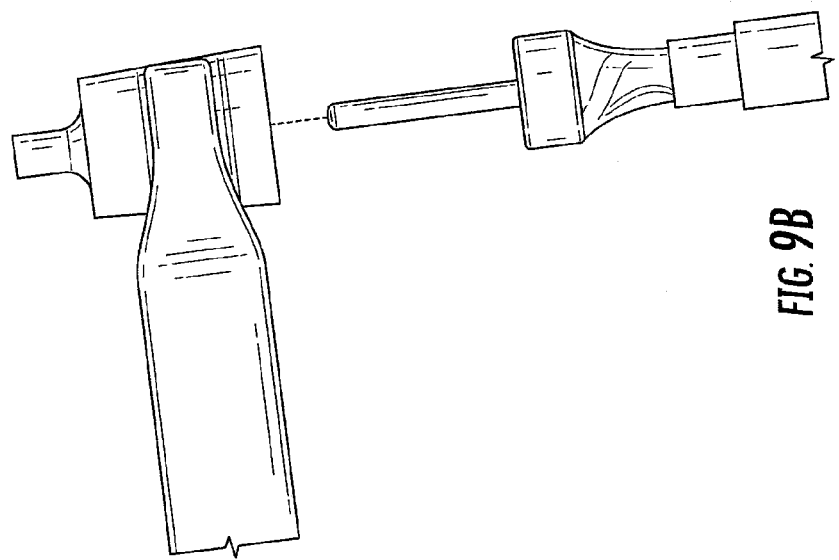
FIGS. 9A-9B are digital images of a side view of a connecting system according to some embodiments of the current invention in a connected position (FIG. 9A) and in a released position (FIG. 9B).
Figure 9A:
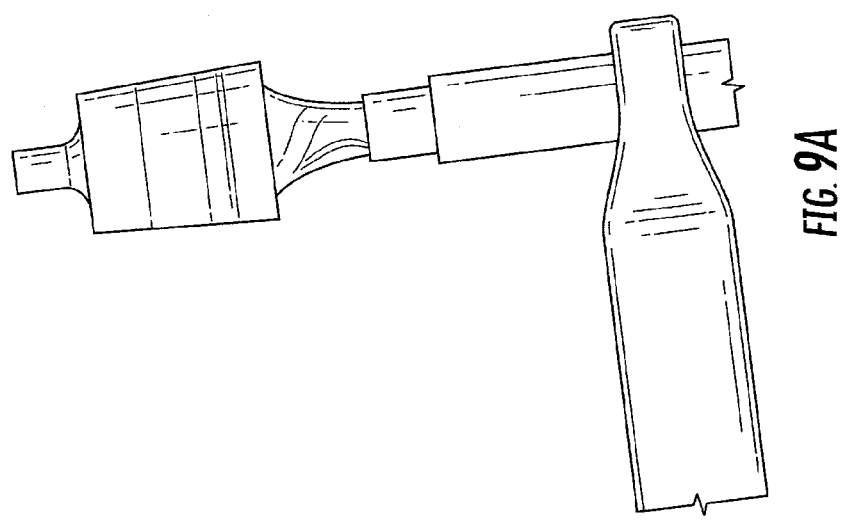
Figure 10A:
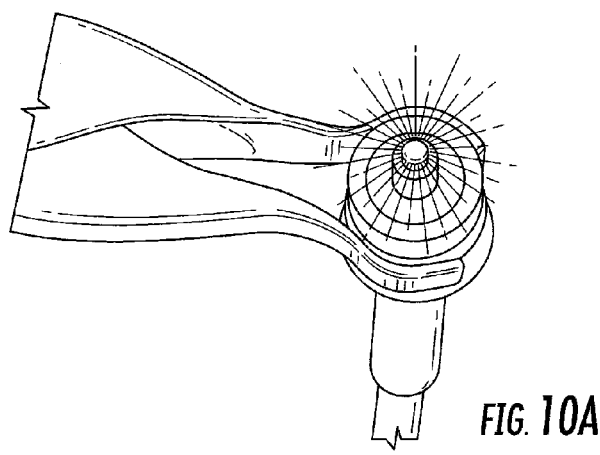
FIGS. 10A-10B are digital images of the connecting system of FIGS. 10A-10B illustrating an end view of the optical fiber output (FIG. 10A) and a top and bottom view of the implantable base unit and interface unit (FIG. 10B).
Figure 10B:
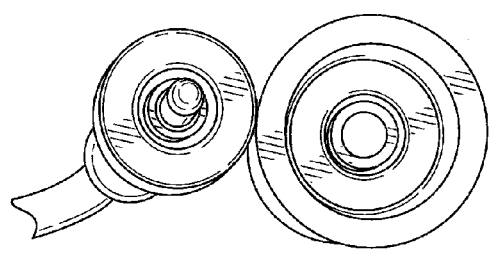
Figure 10C:
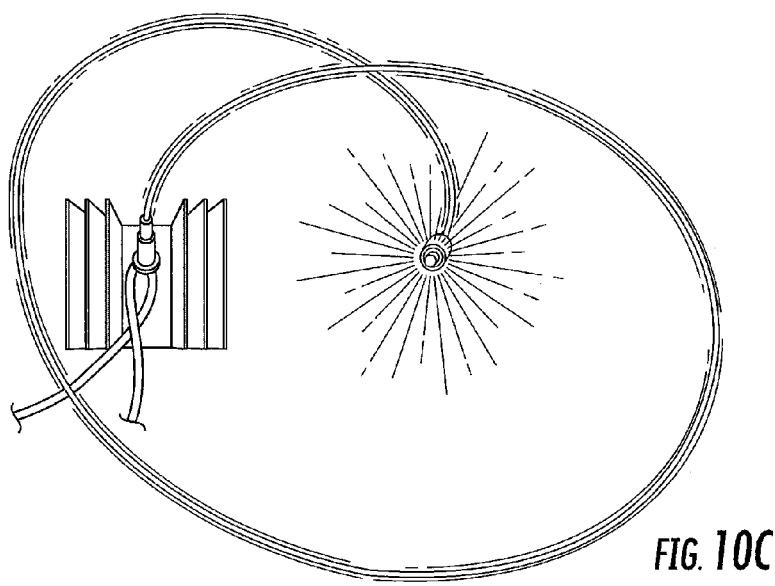
FIG. 10C is a digital image of an external device, such as an LED, that is connected via the connecting system of FIGS. 7A-7B.
Figure 11A:
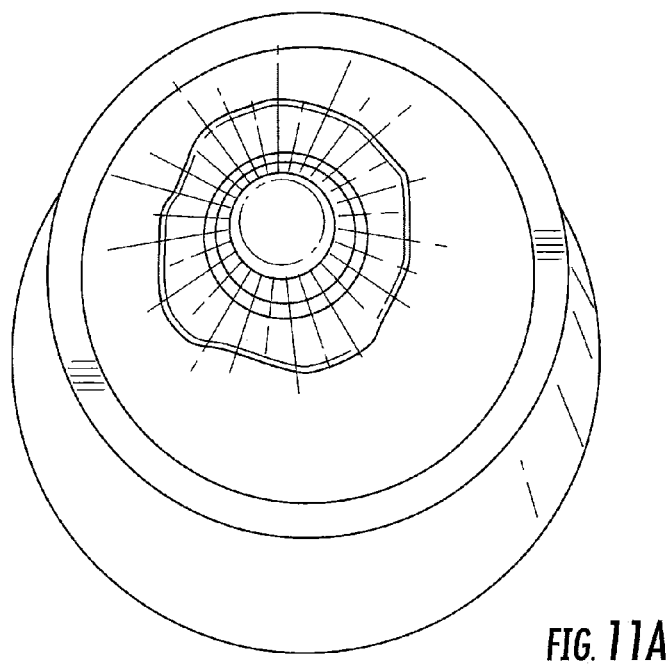
FIGS. 11A-11B are digital images of the connecting system of according to some embodiments illustrating an end view of the optical window mounted on the implantable connector as depicted in FIGS. 6A-6E.
Figure 11B:
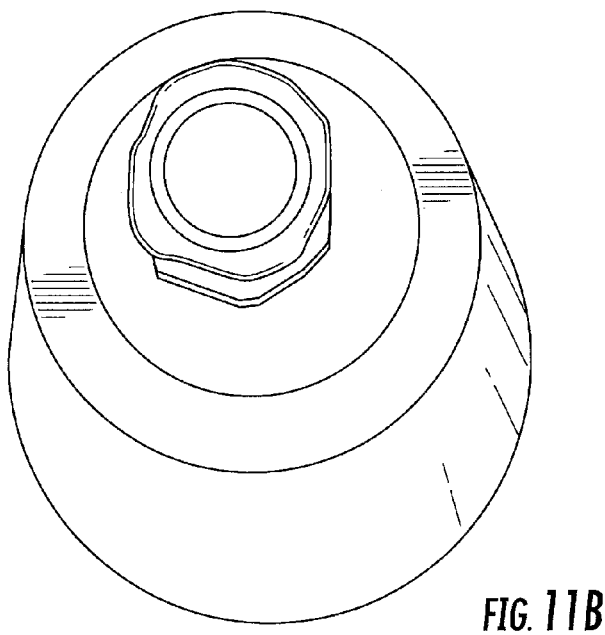
Figure 12A:
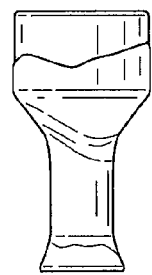
FIGS. 12A-12D are digital images of the connecting system of according to some embodiments illustrating the implantable device (FIG. 12A), the device with the protective cap (FIG. 12B) and magnetic extraction tool (FIG. 12C), which may be used to remove the cap (FIG. 12D), which is also illustrated in FIGS. 8A-8C.
Figure 12B:
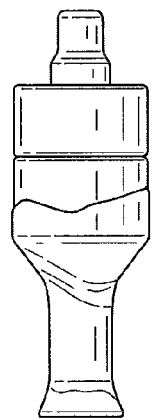
Figure 12C:
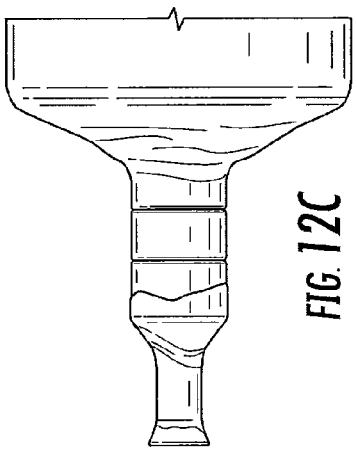
Figure 12D:
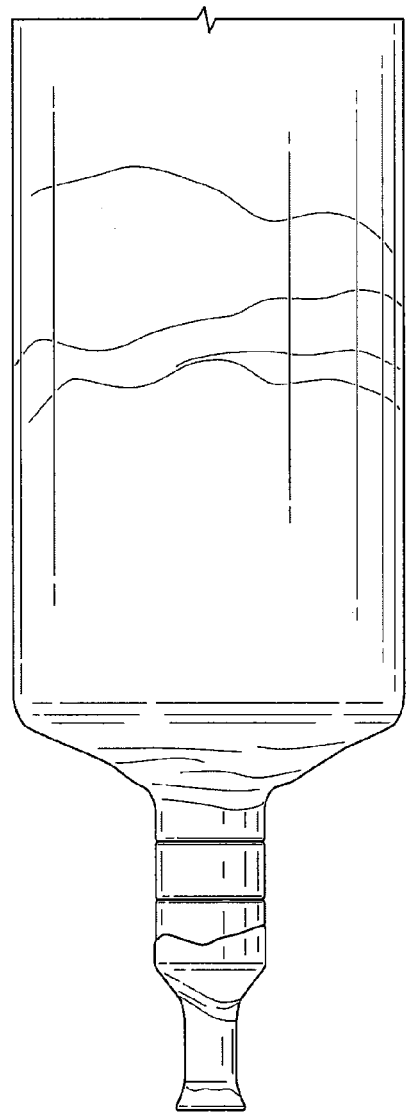

Images of a connector system for use with an optical fiber are shown in FIGS. 9-11. FIGS. 12A-12D illustrates the implantable device (FIG. 12A), the device with the protective cap (FIG. 12B) and magnetic extraction tool (FIG. 12C), which may be used to remove the cap (FIG. 12D).

In addition, the connectors according to embodiments of the present invention may be used to hold and secure other implantable devices, such as probes or multielectrode headstage connectors. In some embodiments, an implantable cannula and an interface cannula may provide a mechanical connection and the implantable cannula does not necessarily provide access to brain or neural tissues. In some embodiments, the implantable cannula/interface cannula may be configured as any suitable mechanically coupled configuration, such as a post/socket connection or other interlocking configuration that may or may not provide a tubular interface or connection, for example, for fiber optics, electrodes or fluid delivery as described herein. Thus, embodiments according to the present invention may provide a combined magnetic and mechanical connection. The post and socket connection described herein may have a circular cross section to allow rotation of the post within the socket; however, in some embodiments, an asymmetrical cross section may be used so that the post fits into the socket in a single orientation. Moreover, in some configurations, the post may be tapered so that the distal end of the post, which is the first portion of the post inserted into the socket, has a smaller diameter than the proximal to facilitate ease of insertion while providing a tighter fit at a wider portion of the post. Other interlocking configurations may include mechanical clips, hooks, snaps or other mechanically interlocking configurations.

Figure 13:
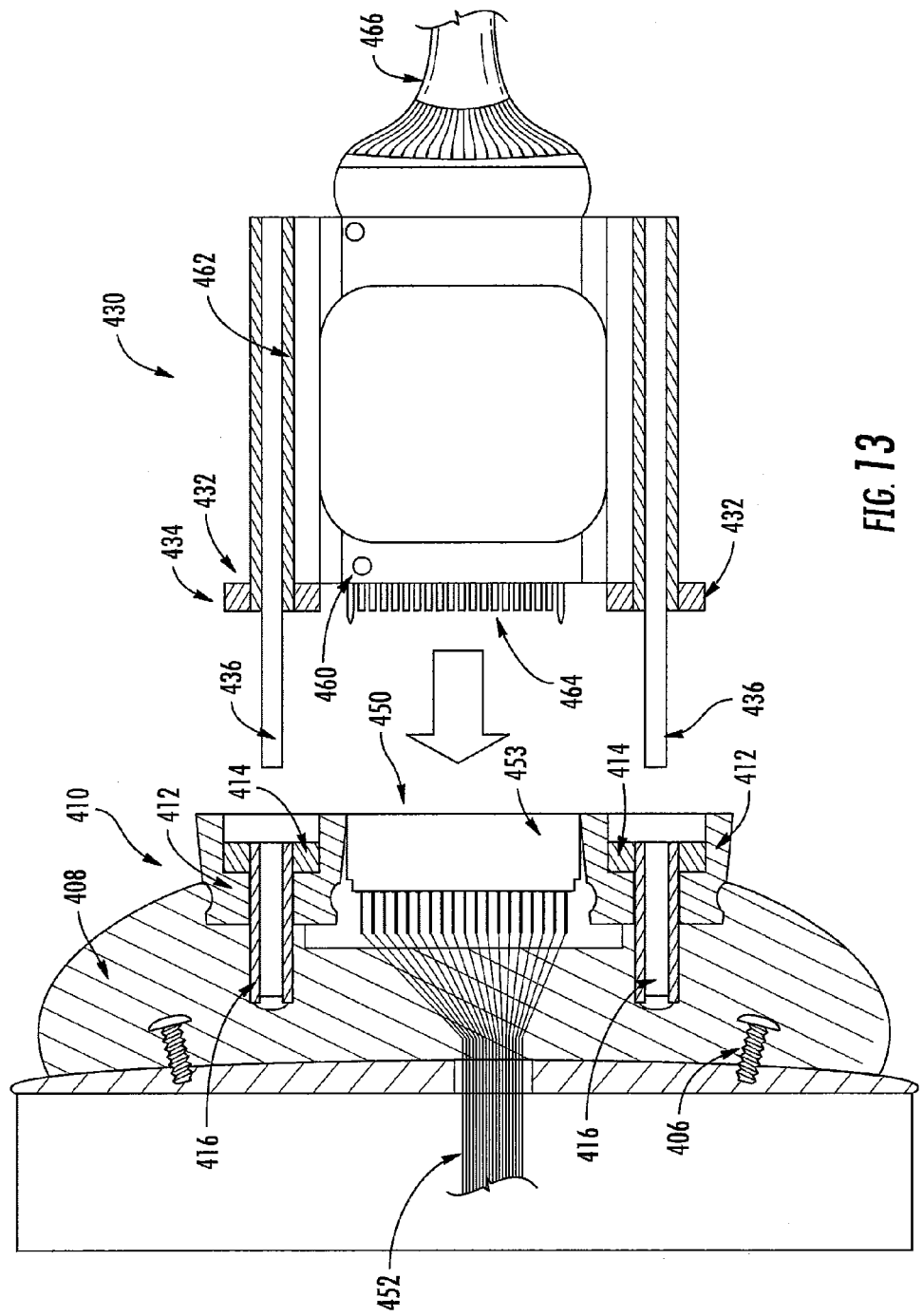
FIG. 13 is a cross sectional view of a connecting system for securing a device in an open configuration according to some embodiments.
Figure 14:
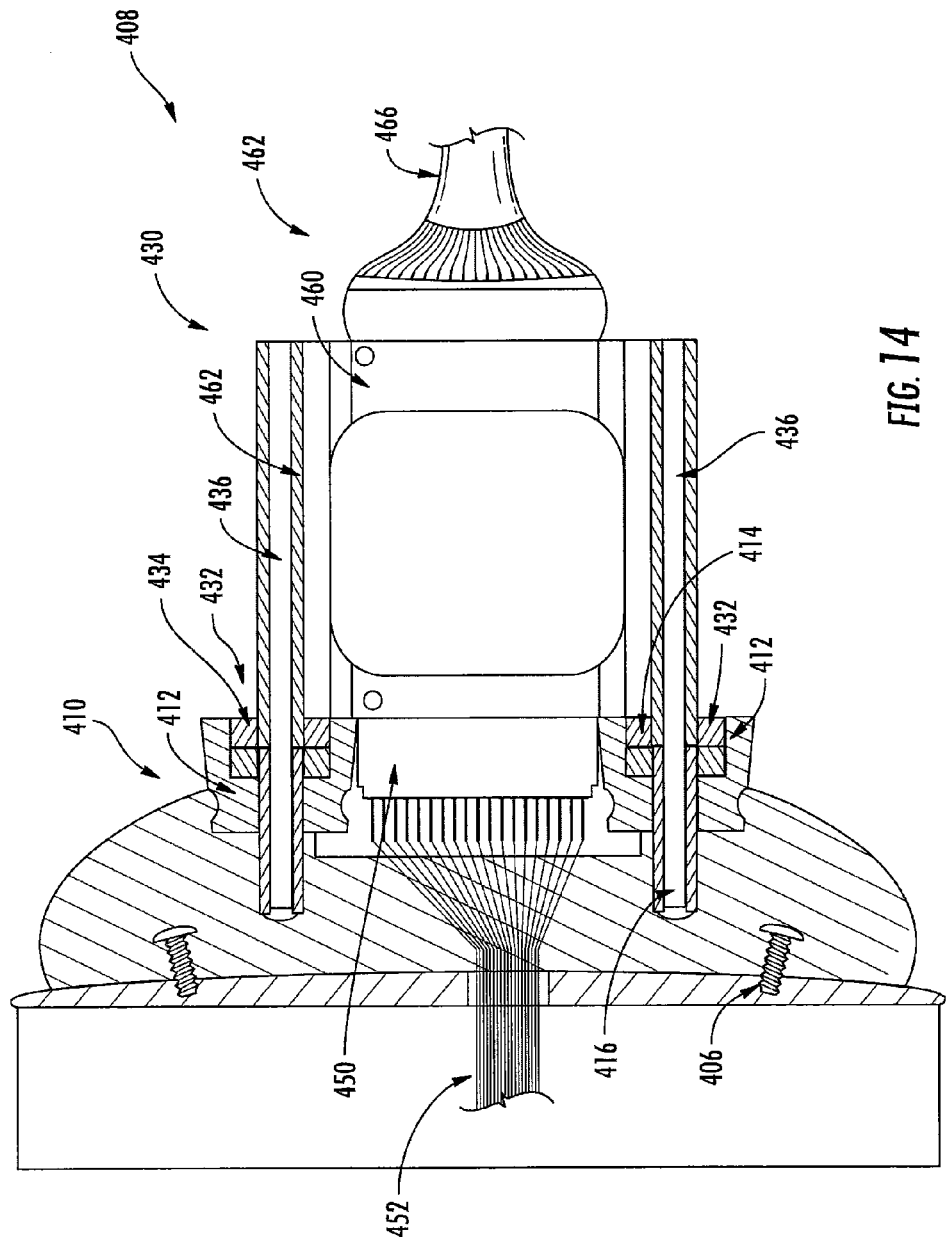
FIG. 14 is a cross sectional view of the connecting system of FIG. 13 in which the implantable base unit is connected to the interface unit.
Figure 15B:
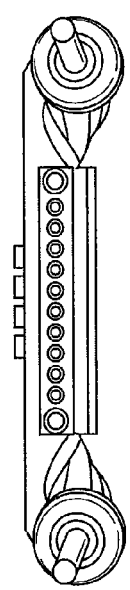
FIG. 15B is a front view of the external interface unit of the connecting system of FIG. 13.
Figure 15D:
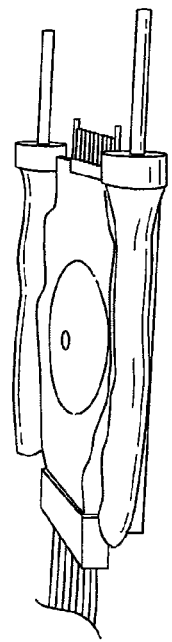
FIG. 15d is a side perspective view of the external interface unit of the connecting system of FIG. 13.
Figure 15A:
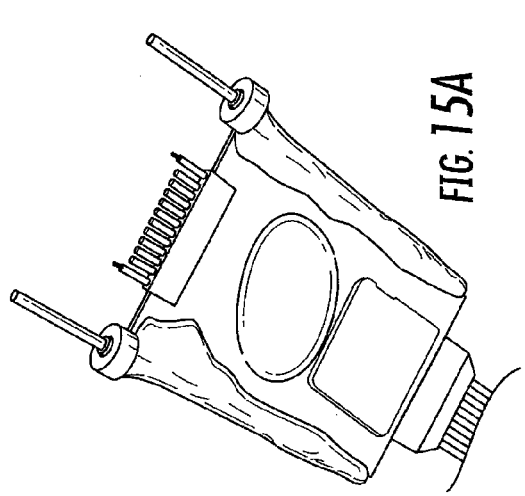
FIG. 15A is a perspective view of the external interface unit of the connecting system of FIG. 13.
Figure 15C:
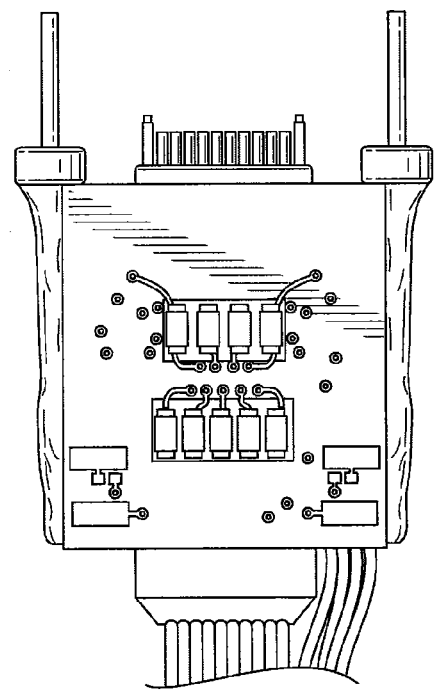
FIG. 15C is a top view of the external interface unit of the connecting system of FIG. 13.
Figure 16A:
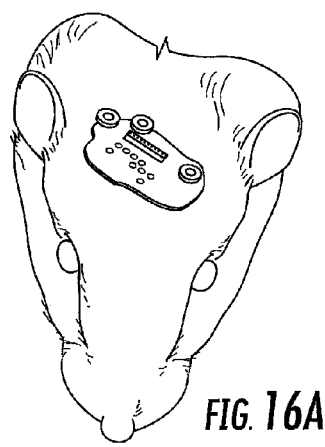
FIGS. 16A-16B are digital images of the implantable unit of the connecting system of FIG. 13 implanted in an animal.
Figure 16B:
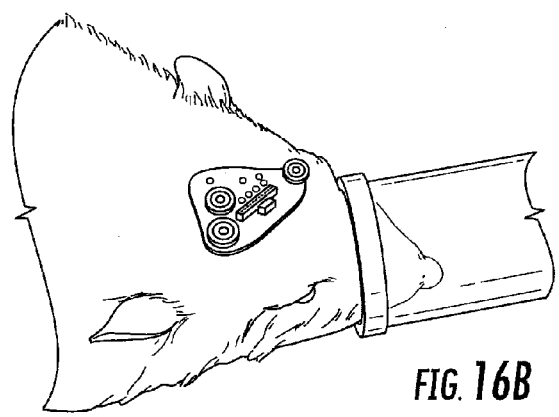
Figure 16C:
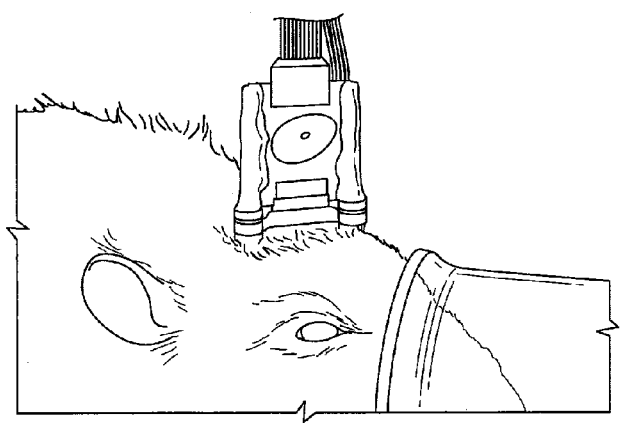
FIG. 16C is a digital image of the connecting system of FIG. 13 implanted in an animal.

For example, as illustrated in FIGS. 13-14, an implantable base unit 410 and interface unit 430 are shown. The base unit 410 includes an implantable electrode assembly 450 and the interface unit 430 includes an external electrode assembly 460. The electrode assemblies 450, 460 may be a custom or commercially available electrode assembly for measuring neurological electrical signals in animals. For example, the implantable electrode assembly 450 may include electrodes 452 that are implanted in or adjacent the brain, other neural tissues (such as the cortex, spinal cord, peripheral nerves), or other tissue from which an electrical signal may be sensed (such as cardiac tissue) and an externally accessible electrode connectors 454. The external electrode assembly 460 may include an amplifier 462 that is configured to amplify the electrical signals from the electrode lines 452, which may be relatively small (such as millivolts), electrical connectors 464 and a cable 466. As illustrated, the connectors 464 are connector pins that are configured to be received in the connectors 453; however, any suitable electrical connector may be used.

In some embodiments, the electrode assemblies 450, 460 may be commercially available assemblies, such as headstages that are available from Plexon, Inc. (Houston, Tex., U.S.A.), Triangle BioSystems, Inc. (Durham, N.C., U.S.A), Tucker Davis Technologies (Alachua, Fla., U.S.A.), or Neuralynx (Bozeman, Mont., U.S.A.) and/or electrical connectors, such as are available from Omnetics Connector Corporation (Minneapolis, Minn., U.S.A.). However, it should be understood that any suitable electrical connector may be used, including custom electrical connectors. The cable 466 may be connected to an additional amplifier and/or a data acquisition unit for acquiring and analyzing the signals from the electrode assemblies 450, 460, such as those available from Plexon, Inc. (Houston, Tex., U.S.A.), Triangle BioSystems, Inc. (Durham, N.C., U.S.A.), Tucker Davis Technologies (Alachua, Fla., U.S.A.), DataWave Technologies (Loveland, Colo., U.S.A.), A-M Systems (Sequim, Wash., U.S.A.) or Neuralynx (Bozeman, Mont., U.S.A).

The implantable base unit 410 includes two implantable housings 412, each having an externally accessible magnetic portion 414 thereon. An implantable, elongated connecting member or socket 416 extends through the housing 412. The implantable base unit 410 is configured to be at least partially implanted in a subject such that the unit 410 is affixed to the skull, and the externally accessible magnetic portion 414 is accessible from an external region of the subject. As further shown in FIG. 13, the implantable base unit 410 and the housings 412 are surgically implanted and affixed to the skull 10 by surgical fasteners, such as screws 406, and biocompatible adhesive such as dental cement 408. As illustrated, the housings 412 are embedded in the cement 408; however, it should be understood that any suitable configuration may be used to affix the housings 412 to the skull. For example, the housings 412 and the cement 408 may be provided as a single unitary member. The interface unit 430 is releasably coupled to the implantable base unit 110.

As shown in FIGS. 13-14, the interface unit 430 includes an interface housing 432 having an interface magnetic portion 434 thereon. An interface elongated, connecting member or post 436 extends through the housing 432. The interface magnetic portion 434 is of a polarity that is opposite the magnetic portion 414 such that the interface magnetic portion 434 attracts and engages the externally accessible magnetic portion 414 of the implantable base unit 410. As shown in FIG. 13, the interface unit 430 may be removed from the cooperating housing 412 of the implantable unit 410. As shown in FIG. 14, the interface magnetic portion 434 and the externally accessible magnetic portion 414 may form a magnetic connection to couple the interface unit 430 and the implantable unit 410. As illustrated, the implantable socket 416 and the interface post 436 are coupled to form a mechanical connection for connecting the interface unit 430 and the implantable unit 410.

In some embodiments, the posts 436 are each formed of a 21 gauge stainless steel wire with a beveled tip, and the sockets 416 are 18 gauge cannulas that are sealed at one end which faces away from the interface unit 430. However the posts 436 and sockets 416 may be any suitable size.

In this configuration, the externally accessible magnetic portion 414 of the implantable unit 410 and the interface unit magnetic portion 434 may connect the implantable unit 410 and the interface unit 430, and the sockets 416 and posts 436 may provide additional mechanical stability to the electrode assemblies 450, 460. The magnetic portions 414, 434 may also provide additional mechanical stability while also permitting the user to disconnect the interface unit 430 from the implantable unit 410 as desired. In some embodiments, the increased mechanical stability may result in a reduction in noise from the electrode assembly 460, and the electrode assemblies 450, 460 may be used for chronic neuro-electrical readings. It should be understood that the housings 412, 432 and the magnetic portions 414, 434 may be configured, for example, as illustrated in FIGS. 1-8 with respect to the housings 112, 132 and magnetic portions 114, 134. Moreover, the implantable base unit 410 may be provided with a pair of protective caps (such as is shown in FIG. 8A) and an extraction tool (such as the extraction tool 300 shown in FIG. 8B) for removing the protective cap. The protective cap may be used to protect the implantable unit 410 when the interface unit 430 is not in use or connected to the implantable unit 410.

Although embodiments are described above with respect to the sockets 416 and posts 436, it should be understood that any suitable mechanically interlocking configuration may be used. In some embodiments, the implantable unit 410 may include a protruding post and the interface unit 430 may include a cannula for receiving the protruding post. Moreover, although the posts 436 are illustrated as having a solid cross section, it should be understood that the posts 436 may be hollow. In some embodiments, a fiber optic or fluid cannula may be used for the post 436, for example, for optogenetics studies, disposable light delivery probes for handheld light sources in medical and dental uses, fluid carrying lines, e.g., for chronic drug or biological delivery to the brain or other organs. Thus, the sockets 416 and posts 436 may be used to provide a cannula with access to the brain or other internal tissue as well as to provide mechanical stability to the electrode assemblies 450, 460.

In some embodiments, the two housings 412 of the implantable unit 410 may be provided as a single, unitary housing and/or the housings 432 of the interface unit 430 may be provided as a single, unitary housing. In some embodiments, the sockets 416 may be rigidly connected to one another by the housings 412 and the posts 436 may be rigidly connected to one another by the housing 432, e.g., for structural stability.

Embodiments according to the present invention will now be described with respect to the following non-limiting example.

EXAMPLE 90-day old Long Evans rats were used for chronic brain inactivation experiments. All procedures were performed in accordance with ACUC guidelines. Under anesthesia, after incision, a small (~1 mm) craniotomy was made and two skull screws were placed adjacently. The dura was reflected and 1 μl of viral vector was injected through the dura into the cortex with a pulled-glass pipet. The pipet was withdrawn and the magnetic connector with cap was lowered into place so that the glass window rested on the surface of the dura. Gel-foam was used to cover any exposed surfaces within the craniotomy. Dental acrylic was used to fix the implanted connector in place and the scalp incision was sutured around the implant. Post-op analgesics were administered while the animal recovered. After 7 days, the animals were adjusted to handling and brief restraint. For each session, the animal was lightly restrained, the protective cap was removed, and the fiber optic was inserted. The animal was then placed in a box for behavioral testing. After the session, the fiber was disconnected, the protective cap was put in place, and the animal was returned to the home cage.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A connecting system comprising:
an implantable base unit having an implantable housing with an externally accessible annular magnetic portion defining an opening therein and an implantable optical fiber in the opening, wherein the implantable base unit is configured to be at least partially implanted in a subject such that the externally accessible annular magnetic portion is accessible from an external region of the subject and the optical fiber is configured to be implanted in the subject; and
an interface unit releasably coupled to the implantable base unit, the interface unit having an interface housing with an annular interface magnetic portion on an external surface of the interface housing and defining an opening therein, the interface unit further comprising an interface optical fiber in the opening of the annular interface magnetic portion and extending into the housing, wherein the annular interface magnetic portion is configured to engage the externally accessible annular magnetic portion of the implantable base unit to mechanically couple the implantable optical fiber and the interface optical fiber,
wherein the interface magnetic portion and the externally accessible magnetic portion form a rotatable coupling therebetween to rotatably couple the interface unit to the implantable base unit such that respective surfaces of the interface magnetic portion and the externally accessible magnetic portion rotate with respect to one another while maintaining an optical connection between the implantable optical fiber and the interface optical fiber.

2. The connecting system of claim 1, wherein the implantable optical fiber is configured to optically stimulate a portion of a brain of the subject.

3. The connecting system of claim 1, wherein the interface optical fiber is configured to connect to an external light source and to provide a light passageway for light from the external light source to the implantable optical fiber.

4. The connecting system of claim 1, further comprising a buffer material on the interface unit configured to provide a buffer region around the interface magnetic portion and the externally accessible magnetic portion.

5. The connecting system of claim 1, wherein the interface unit comprises an interface cannula with the interface optical fiber in the interface cannula.

6. The connecting system of claim 1, wherein the interface unit comprises an interface cannula with the interface optical fiber in the interface cannula, the implantable optical fiber is connected to the interface cannula and is removably inserted in the implantable cannula, and the implantable cannula further comprises an optical window or lens on an end of the implantable cannula that is configured to transmit light from the implantable optical fiber to the subject when the interface unit is connected to the implantable unit.

7. The connecting system of claim 1, further comprising a removable cover that is configured to be removably received in the implantable base unit and to cover the implantable optical fiber when the interface unit is removed from the implantable base unit.

8. The connecting system of claim 7, wherein the removable cover comprises a magnetic portion that is configured to mate with the externally accessible magnetic portion when the removable cover is received in the implantable base unit, and the magnetic portion of the removable cover is further configured to mate with a magnetic portion of an extraction tool so as to remove the removable cover from the implantable base unit.

9. The connecting system of claim 7, wherein the removable cover comprises a first end configured to be inserted into the implantable base unit and a second end opposite the first end, wherein the second end comprises a magnetic portion.

10. The connecting system of claim 9, further comprising an extraction tool comprising a magnetic portion on an end thereof that is configured to engage the magnetic portion on the second end of the removable cover to thereby remove the removable cover from the implantable base unit when the extraction tool is moved away from the implantable base unit.

11. The connecting system of claim 1, wherein the implantable housing comprises a first implantable housing, the externally accessible magnetic portion comprises a first magnetic portion, the opening of the externally accessible annular magnetic portion comprises a first implantable unit connecting member, the interface housing comprises a first interface housing, the interface magnetic portion comprises a first interface magnetic portion and the opening of the annular interface magnetic portion comprises a first connecting member,
wherein the implantable base unit further comprises a second implantable housing with a second externally accessible magnetic portion and a second implantable unit connecting member, and
wherein the interface unit further comprises a second interface housing with a second interface magnetic portion and a second interface unit connecting member, wherein the second interface magnetic portion is configured to engage the second externally accessible magnetic portion of the implantable base unit to mechanically couple the second implantable unit connecting member and the second interface unit connecting member.

12. The connecting system of claim 11, wherein the first and second implantable housings are rigidly connected.

13. The connecting system of claim 11, wherein the first and second interface housings are rigidly connected.

14. A connection method comprising:
providing an implantable base unit having an implantable housing with an externally accessible annular magnetic portion defining an opening therein and an implantable optical fiber in the opening, wherein the implantable base unit is configured to be at least partially implanted in a subject such that the externally accessible annular magnetic portion is accessible from an external region of the subject and the optical fiber is configured to be implanted in the subject;
providing an interface unit having an interface housing with an annular interface magnetic portion on an external surface of the interface housing and defining an opening therein, the interface unit further comprising an interface optical fiber; and
engaging the externally accessible annular magnetic portion of the implantable base unit with the interface annular magnetic portion of the interface unit to rotatably couple the implantable optical fiber and the interface optical fiber, wherein the interface magnetic portion and the externally accessible magnetic portion form a rotatable coupling therebetween to rotatably couple the interface unit to the implantable base unit such that respective surfaces of the interface magnetic portion and the externally accessible magnetic portion rotate with respect to one another while maintaining an optical connection between the implantable optical fiber and the interface optical fiber.

15. A connection method comprising:
implanting an implantable base unit in a subject, the implantable base unit having an implantable housing with an externally accessible annular magnetic portion defining an opening therein and an implantable optical fiber in the opening, such that the externally accessible annular magnetic portion is accessible from an external region of the subject and the optical fiber is configured to be implanted in the subject; and
connecting an interface unit to the implantable unit, the interface unit having an interface housing with an annular interface magnetic portion on an external surface of the interface housing and defining an opening therein, the interface unit further comprising an optical fiber in the opening of the annular interface magnetic portion extending into the housing, wherein the annular interface magnetic portion mechanically engages the externally accessible annular magnetic portion of the implantable base unit to rotatably couple the implantable optical fiber and the interface unit optical fiber, wherein the annular interface magnetic portion and the externally accessible annular magnetic portion form a rotatable coupling therebetween to rotatably couple the interface unit to the implantable base unit such that respective surfaces of the annular interface magnetic portion and the externally accessible annular magnetic portion rotate with respect to one another while maintaining an optical connection between the implantable optical fiber and the interface unit optical fiber,
wherein the implantable unit comprises an implantable cannula with the implantable optical fiber in the implantable cannula, the method further comprising:
positioning the interface unit optical fiber in the implantable cannula to connect to the implantable base unit, the method further comprising connecting a light source to the implantable optical fiber to illuminate a region of the brain.

* * * * *